US012802827B2

(12) United States Patent
Hubenov et al.

(10) Patent No.: US 12,802,827 B2
(45) Date of Patent: Nov. 17, 2026

(54) INFRASTRUCTURE SELECTION FOR MEDICAL APPLICATIONS

(71) Applicant: Align Technology, Inc., San Jose, CA (US)

(72) Inventors: Svetozar Grigorov Hubenov, Lucerne (CH); Leela Mohan Parvathaneni, San Jose, CA (US); Sravani Gurijala, Apex, NC (US); Bandhavi Nalajala, Durham, NC (US); Irina Ivanova, Rotkreutz (CH)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 18/935,174

(22) Filed: Nov. 1, 2024

(65) Prior Publication Data

US 2025/0149189 A1 May 8, 2025

Related U.S. Application Data

(60) Provisional application No. 63/596,213, filed on Nov. 3, 2023.

(51) Int. Cl.
*G16H 80/00* (2018.01)
*G16H 10/60* (2018.01)
*G16H 30/20* (2018.01)

(52) U.S. Cl.
CPC ............ *G16H 80/00* (2018.01); *G16H 10/60* (2018.01); *G16H 30/20* (2018.01)

(58) Field of Classification Search
CPC ........ G16H 80/00; G16H 10/60; G16H 30/20; G16H 30/40; G16H 20/40; G16H 40/67; G16H 50/20; G16H 50/70
See application file for complete search history.

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |
| 6,227,851 | B1 | 5/2001 | Chishti et al. |
| 6,299,440 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |
| 6,406,292 | B1 | 6/2002 | Chishti et al. |
| 6,409,504 | B1 | 6/2002 | Jones et al. |
| 6,457,972 | B1 | 10/2002 | Chishti et al. |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |
| 6,621,491 | B1 | 9/2003 | Baumrind et al. |
| 6,688,886 | B2 | 2/2004 | Hughes et al. |

(Continued)

*Primary Examiner* — Richard G Keehn

(74) *Attorney, Agent, or Firm* — Lowenstein Sandler LLP

(57) ABSTRACT

Embodiments include receiving one or more patient case details of a patient, receiving one or more images of a dentition of the patient, selecting an infrastructure from a plurality of infrastructures based on the one or more patient case details, processing the one or more images using logic of the selected infrastructure, wherein the logic outputs dental treatment information for the patient, and sending the dental treatment information to a remote computing device.

20 Claims, 5 Drawing Sheets

(56) References Cited

U.S. PATENT DOCUMENTS 6,726,478 B1 4/2004 Isiderio et al.
6,729,876 B2 5/2004 Chishti et al.
6,739,869 B1 5/2004 Taub et al.
6,767,208 B2 7/2004 Kaza
6,783,360 B2 8/2004 Chishti
7,040,896 B2 5/2006 Pavlovskaia et al.
7,063,532 B1 6/2006 Jones et al.
7,074,038 B1 7/2006 Miller
7,074,039 B2 7/2006 Kopelman et al.
7,077,647 B2 7/2006 Choi et al.
7,108,508 B2 9/2006 Hedge et al.
7,134,874 B2 11/2006 Chishti et al.
7,156,661 B2 1/2007 Choi et al.
7,160,107 B2 1/2007 Kopelman et al.
7,241,142 B2 7/2007 Abolfathi et al.
7,293,988 B2 11/2007 Wen
7,357,634 B2 4/2008 Knopp
7,555,403 B2 6/2009 Kopelman et al.
7,637,740 B2 12/2009 Knopp
7,689,398 B2 3/2010 Cheng et al.
7,736,147 B2 6/2010 Kaza et al.
7,746,339 B2 6/2010 Matov et al.
7,844,356 B2 11/2010 Matov et al.
7,844,429 B2 11/2010 Matov et al.
7,865,259 B2 1/2011 Kuo et al.
7,878,804 B2 2/2011 Korytov et al.
7,880,751 B2 2/2011 Kuo et al.
7,904,308 B2 3/2011 Arnone et al.
7,930,189 B2 4/2011 Kuo
7,942,672 B2 5/2011 Kuo
7,970,627 B2 6/2011 Kuo et al.
7,970,628 B2 6/2011 Kuo et al.
8,038,444 B2 10/2011 Kitching et al.
8,044,954 B2 10/2011 Kitching et al.
8,075,306 B2 12/2011 Kitching et al.
8,092,215 B2 1/2012 Stone-Collonge et al.
8,099,268 B2 1/2012 Kitching et al.
8,108,189 B2 1/2012 Chelnokov et al.
8,126,726 B2 2/2012 Matov et al.
8,260,591 B2 9/2012 Kass et al.
8,275,180 B2 9/2012 Kuo
8,401,826 B2 3/2013 Cheng et al.
8,439,672 B2 5/2013 Matov et al.
8,562,338 B2 10/2013 Kitching et al.
8,591,225 B2 11/2013 Wu et al.
8,788,285 B2 7/2014 Kuo
8,843,381 B2 9/2014 Kuo et al.
8,874,452 B2 10/2014 Kuo
8,896,592 B2 11/2014 Boltunov et al.
8,930,219 B2 1/2015 Trosien et al.
9,037,439 B2 5/2015 Kuo et al.
9,060,829 B2 6/2015 Sterental et al.
9,125,709 B2 9/2015 Matty
9,211,166 B2 12/2015 Kuo et al.
9,220,580 B2 12/2015 Borovinskih et al.
9,364,296 B2 6/2016 Kuo
9,375,300 B2 6/2016 Matov et al.
9,414,897 B2 8/2016 Wu et al.
9,492,245 B2 11/2016 Sherwood et al.
9,642,678 B2 5/2017 Kuo
10,248,883 B2 4/2019 Borovinskih et al.
10,342,638 B2 7/2019 Kitching et al.
10,463,452 B2 11/2019 Matov et al.
10,595,966 B2 3/2020 Carrier, Jr. et al.
10,617,489 B2 4/2020 Grove et al.
10,722,328 B2 7/2020 Velazquez et al.
10,779,718 B2 9/2020 Meyer et al.
10,792,127 B2 10/2020 Kopelman et al.
10,835,349 B2 11/2020 Cramer et al.
10,973,611 B2 4/2021 Pokotilov et al.
10,996,813 B2 5/2021 Makarenkova et al.
10,997,727 B2 5/2021 Xue et al.
11,020,205 B2 6/2021 Li et al.
11,020,206 B2 6/2021 Shi et al.
11,026,766 B2 6/2021 Chekh et al.
11,033,359 B2 6/2021 Velazquez et al.
11,071,608 B2 7/2021 Derakhshan et al.
11,096,763 B2 8/2021 Akopov et al.
11,116,605 B2 9/2021 Nyukhtikov et al.
11,147,652 B2 10/2021 Mason et al.
11,151,753 B2 10/2021 Gao et al.
11,154,381 B2 10/2021 Roschin et al.
11,259,896 B2 3/2022 Matov et al.
11,357,598 B2 6/2022 Cramer
11,395,717 B2 7/2022 Yuryev et al.
11,432,908 B2 9/2022 Kopelman et al.
11,464,604 B2 10/2022 Makarenkova et al.
11,478,334 B2 10/2022 Matov et al.
11,484,389 B2 11/2022 Sterental et al.
11,534,272 B2 12/2022 Li et al.
11,553,988 B2 1/2023 Mednikov et al.
11,633,268 B2 4/2023 Moalem et al.
11,642,195 B2 5/2023 Gao et al.
11,651,494 B2 5/2023 Brown et al.
11,654,001 B2 5/2023 Roschin et al.
11,707,344 B2 7/2023 Roschin et al.
11,723,748 B2 8/2023 Li et al.
11,810,271 B2 11/2023 Shi et al.
11,850,111 B2 12/2023 Derakhshan et al.
11,864,970 B2 1/2024 Shojaei et al.
11,903,793 B2 2/2024 Cramer et al.
11,978,547 B2 5/2024 Levin et al.
12,023,216 B2 7/2024 Pimenov et al.
12,048,604 B2 7/2024 Roschin et al.
12,048,605 B2 7/2024 Farkash et al.
12,076,207 B2 9/2024 Liu et al.
12,090,020 B2 9/2024 Cramer
12,106,845 B2 10/2024 Meyer et al.
12,125,581 B2 10/2024 Slynko et al.
12,193,905 B2 1/2025 Chekhonin et al.
12,220,288 B2 2/2025 Chekh et al.
2003/0008259 A1 1/2003 Kuo et al.
2003/0143509 A1 7/2003 Kopelman et al.
2003/0207227 A1 11/2003 Abolfathi
2004/0137400 A1 7/2004 Chishti et al.
2004/0152036 A1 8/2004 Abolfathi
2004/0197728 A1 10/2004 Abolfathi et al.
2004/0259049 A1 12/2004 Kopelman et al.
2005/0182654 A1 8/2005 Abolfathi et al.
2005/0244791 A1 11/2005 Davis et al.
2006/0127836 A1 6/2006 Wen
2006/0127852 A1 6/2006 Wen
2006/0127854 A1 6/2006 Wen
2006/0275731 A1 12/2006 Wen et al.
2006/0275736 A1 12/2006 Wen et al.
2008/0306724 A1 12/2008 Kitching et al.
2010/0009308 A1 1/2010 Wen et al.
2010/0068672 A1 3/2010 Arjomand et al.
2010/0068676 A1 3/2010 Mason et al.
2010/0092907 A1 4/2010 Knopp
2010/0167243 A1 7/2010 Spiridonov et al.
2013/0204599 A1 8/2013 Matov et al.
2017/0273760 A1 9/2017 Morton et al.
2022/0023002 A1 1/2022 Cramer et al.
2022/0079714 A1 3/2022 Paraketsov et al.
2022/0104920 A1 4/2022 Wang et al.
2022/0130532 A1* 4/2022 Lemchen ............... G16H 30/40
2022/0165388 A1 5/2022 Chernov et al.
2022/0202295 A1 6/2022 Elbaz et al.
2022/0262007 A1 8/2022 Cramer et al.
2022/0331062 A1* 10/2022 Crutchfield ............ G16H 20/40
2022/0378549 A1 12/2022 Blanco et al.
2023/0008836 A1 1/2023 Yazykov et al.
2023/0056427 A1 2/2023 Blanco et al.
2023/0072074 A1* 3/2023 Oda ......................... A61C 7/20
2023/0072470 A1* 3/2023 Miller .................. H04N 23/611
2023/0149129 A1* 5/2023 Oren-Artzi ............ G16H 30/40
2023/0190411 A1 6/2023 Chiu et al.
2023/0225831 A1 7/2023 Cramer et al.
2023/0263594 A1 8/2023 Lobsiger et al.
2023/0301752 A1 9/2023 Wang et al.
2023/0325558 A1 10/2023 Kukk et al.
2023/0352150 A1 11/2023 Meyer et al.
2023/0414323 A1 12/2023 Sun et al.

(56) References Cited

U.S. PATENT DOCUMENTS

| | | | | |
|---|---|---|---|---|
| 2024/0023800 | A1* | 1/2024 | Fridman | G16H 30/40 |
| 2024/0033041 | A1 | 2/2024 | Chernov et al. | |
| 2024/0033045 | A1 | 2/2024 | Tanugula et al. | |
| 2024/0065807 | A1 | 2/2024 | Chang et al. | |
| 2024/0087184 | A1 | 3/2024 | Gao et al. | |
| 2024/0108436 | A1 | 4/2024 | Grebenkin et al. | |
| 2024/0122463 | A1 | 4/2024 | Li et al. | |
| 2024/0122677 | A1 | 4/2024 | Popov et al. | |
| 2024/0131795 | A1 | 4/2024 | Li et al. | |
| 2024/0144480 | A1 | 5/2024 | Seeber et al. | |
| 2024/0177397 | A1 | 5/2024 | Li et al. | |
| 2024/0185420 | A1 | 6/2024 | Cramer et al. | |
| 2024/0185518 | A1 | 6/2024 | Seeber et al. | |
| 2024/0189078 | A1 | 6/2024 | Cramer et al. | |
| 2024/0197449 | A1 | 6/2024 | Stroganov et al. | |
| 2024/0216106 | A1 | 7/2024 | Choi et al. | |
| 2024/0257342 | A1 | 8/2024 | Semenov et al. | |
| 2024/0277450 | A1 | 8/2024 | Sherstennikov et al. | |
| 2024/0293200 | A1 | 9/2024 | Kirsanov et al. | |
| 2025/0079001 | A1* | 3/2025 | Bergersen | G16H 50/20 |
| 2025/0218590 | A1* | 7/2025 | Derzapf | G16H 50/20 |
| 2025/0378939 | A1* | 12/2025 | Jellinggaard | G16H 30/20 |

* cited by examiner

INFRASTRUCTURE SELECTION FOR MEDICAL APPLICATIONS

RELATED APPLICATIONS

This patent application claims the benefit under 35 U.S.C. § 119(e) of U.S. Provisional Application No. 63/596,213, filed Nov. 3, 2023, which is incorporated by reference herein.

TECHNICAL FIELD

Embodiments of the present disclosure relate to the field of medical software and, in particular, to infrastructure selection for a medical application.

BACKGROUND

Medical software such as that used to develop treatment plans for patients or perform treatments on the patients is regulated under a strict set of safety regulations. For example, software as a medical device (SaMD) is software that performs one or more medical functions, and is regulated by various agencies. Regulations for medical software may impose constraints on when a version of the software can be used on patients, on who can use the version of the software, and so on. Many countries have their own regulations on medical software. Accordingly, it can be difficult for a medical application to comply with the regulations of multiple different countries.

SUMMARY

In a first example implementation, a system comprises: a computing device comprising a memory and one or more processing devices, wherein the computing device is configured to: receive one or more patient case details of a patient; receive one or more images of a dentition of the patient; select an infrastructure from a plurality of infrastructures based at least in part on the one or more patient case details; process the one or more images logic of the selected infrastructure, wherein the logic outputs dental treatment information for the patient; and send the dental treatment information to a remote computing device.

In a second example implementation, a non-transitory computer readable medium comprises instructions that, when executed by one or more processing devices, cause the one or more processing devices to perform operations comprising: receiving one or more patient case details of a patient; receiving one or more images of a dentition of the patient; selecting a machine learning model infrastructure from a plurality of machine learning model infrastructures based at least in part on the one or more patient case details; processing the one or more images using one or more trained machine learning models of the selected machine learning model infrastructure, wherein the one or more trained machine learning models output dental treatment information for the patient; and sending the dental treatment information to a remote computing device.

In a third example implementation, a method comprises: receiving one or more patient case details of a patient; receiving one or more images of a dentition of the patient; selecting an infrastructure from a plurality of infrastructures based at least in part on the one or more patient case details; processing the one or more images using one or more models of the selected machine infrastructure, wherein the one or more models output dental treatment information for the patient; and sending the dental treatment information to a remote computing device.

BRIEF DESCRIPTION OF THE DRAWINGS

Embodiments of the present disclosure are illustrated by way of example, and not by way of limitation, in the figures of the accompanying drawings.

DETAILED DESCRIPTION

Figure 1A:
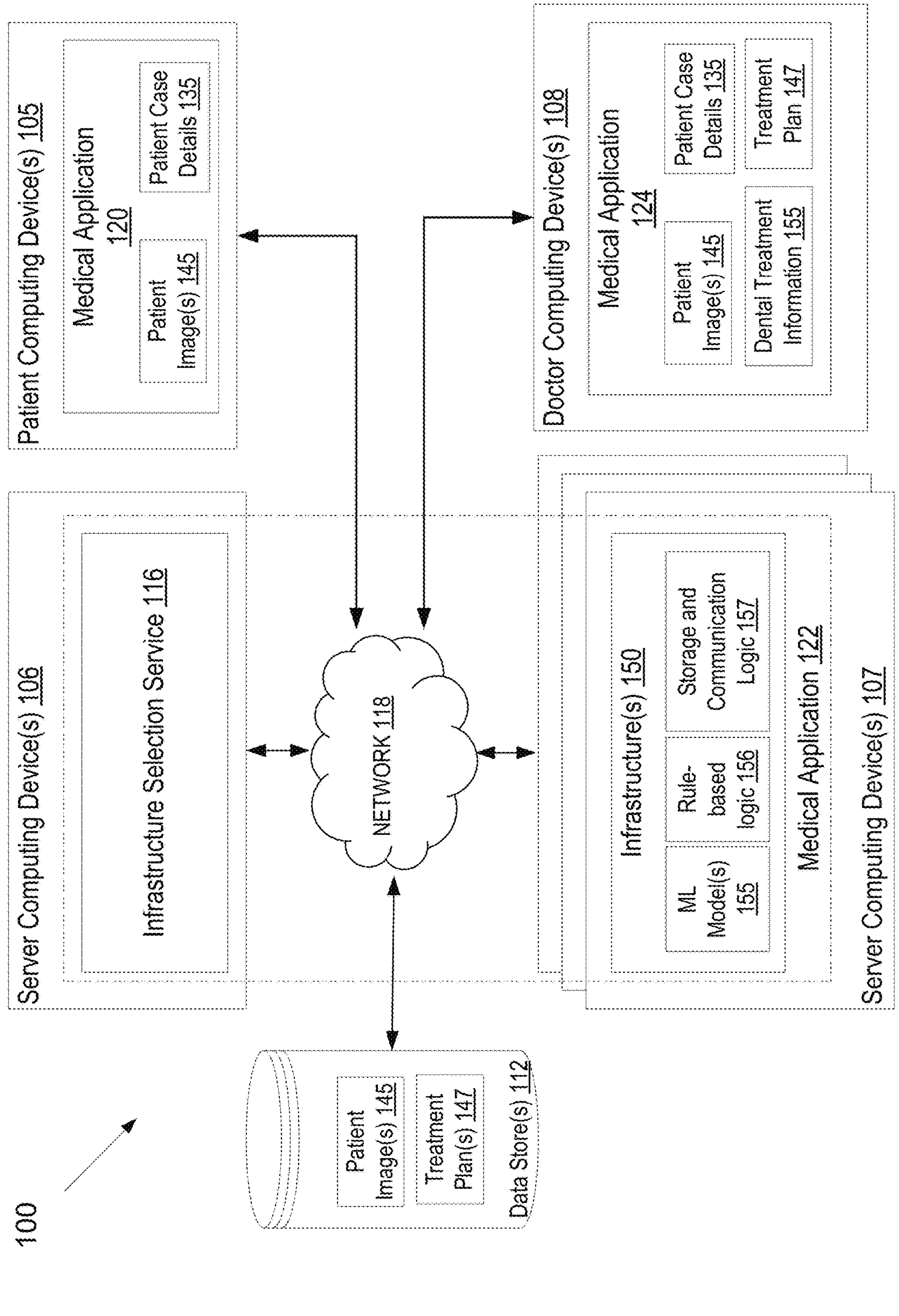
FIG. 1A illustrates one embodiment of a system for executing medical applications, in accordance with an embodiment.

Described herein are methods and systems for selecting an infrastructure for a medical application to apply in assessment of a patient medical condition (e.g., a dental condition) for a patient case, in accordance with embodiments of the present disclosure. In some embodiments, the selected infrastructure is or includes a machine learning model infrastructure. Alternatively, or additionally, the selected infrastructure may be or include an application infrastructure, a cloud infrastructure, and/or other type of infrastructure. For example, embodiments also cover medical application infrastructure selection. Embodiments cover an infrastructure selection service, which may apply one or more rules to select an appropriate infrastructure (e.g., a machine learning model infrastructure, medical application infrastructure, etc.) to use for processing patient data. The one or more rules may be used to select an infrastructure based on region or location of a patient, based on a practice of doctor of the patient, based on a patient type (e.g., child vs. adult), based on a type of treatment to be performed, and/or based on other patient case details. Different machine learning model infrastructures and/or medical application infrastructures (and/or other type of infrastructures) may each include different servers, data stores, trained machine learning models, and so on, and/or may be located in different locations. For example, a first infrastructure may be located in Europe and may be used for processing patient data of patients in European countries, a second infrastructure may be located in China and may be used for processing patient data of patients in China, a third infrastructure may be located in the United States and may be used to process patient data of patients in the United States, and so on.

Medical applications and other medical software is subject to various regulations to ensure patient safety, data security, and the effectiveness of healthcare technology. Specific regulations vary based on country or region. In the United States (US), the Food and Drug Administration (FDA) regulates medical software under the Federal Food, Drug and Cosmetic Act (FD&C Act). Software that meets the definition of a medical device is subject to FDA oversight. Depending on the risk level, medical software may require premarket clearance (e.g., 510(k) clearance) or approval (e.g., Pre-market Approval-PMA) before it can be marketed. As new versions of the medical software are generated each time configuration settings of products offered by the medical software are modified, each such version may need to undergo rigorous testing before it can be released for general use in the US. Similarly, medical devices regulation (MDR) in the European Union provides regulations for medical devices, including software, within the European Union. Medical software must meet the requirements outlined in the MDR and may need to undergo conformity assessment procedures, such as certification by a notified body, based on the software's classification. Additionally, the International Medical Device Regulators Forum (IMDRF) is a global organization that harmonizes medical device regulations. The IMDF has released guidance documents related to software as a medical device (SaMD), providing recommendations on risk categorization, clinical evaluation, and cybersecurity. A commonality of each of the regulating bodies for medical applications/software is an imposition of additional rules and regulations for medical applications/software that do not exist for other types of applications/software.

Additionally, different countries have different regulations with regards to handling of patient data, storage of patient data, and so on. In example, the United States has multiple rules on maintaining the privacy of patient data under the Health Insurance Portability and Accountability Act (HIPAA). Other countries has similar regulations. Many countries also have regulations on the use of artificial intelligence and machine learning for one or more purposes.

Embodiments of the present disclosure address the many and varied regulations of different countries and/or regional blocs of countries with regards to management of patient data, medical applications and machine learning models by maintaining multiple different infrastructures (e.g., machine learning model infrastructures) in parallel. The various infrastructures may be configured to perform the same or similar operations, but may be tailored to comply with the many regulations of different countries or regional blocs of countries. An infrastructure selection service may process incoming requests and select an appropriate infrastructure, from the multiple available infrastructures, that will comply with the regulations of the country or regional block of countries in which a patient associated with an incoming request is located. In this manner, a provider of a medical application may ensure that the medical application complies with all of the regulatory requirements of each of the countries in which the medical application is used without having to design separate medical applications for each of those countries or regional bloc of countries.

Traditionally, in order to change existing machine learning-based products (also referred to herein as treatment types or offerings) provided by a medical application, one or more trained machine learning models may be modified for those products in the medical application. Such changes to the medical application cause a new version of the medical application to be generated, which is then tested before the new version of the medical application can be deployed to and installed on computing devices used in production. For medical applications that will be used in multiple countries, the updated medical application should generally be submitted for approval to the regulatory bodies of those multiple countries. Only when all of the regulatory bodies have approved the updated medical application (e.g., the updated trained machine learning models of the medical application), can the updated medical application be released into production. In embodiments, different infrastructures (e.g., machine learning model infrastructures) may each have a same update to a medical application and/or to one or more machine learning models. Each of the infrastructures may be associated with a different country or regional bloc of countries. As soon as the regulatory body of any country or regional bloc of countries approves the updated medical application and/or updated trained machine learning models of the medical application, the updated medical application and/or machine learning models for the infrastructure associated with that country or regional bloc may be released into a production environment, even though other countries may not have approved the updated medical application and/or machine learning models yet. Accordingly, updates to medical applications and/or machine learning models of medical applications may be released more quickly than is traditionally possible in some countries.

Embodiments provide an infrastructure selection service (e.g., a machine learning model selection service) that may be a cloud-based service and/or that may be integrated into a medical application that executes on a user device (e.g., on a computing device of a patient) to select an infrastructure (e.g., a machine learning model infrastructure) to use for a patient case. The infrastructure selection service may receive patient data and/or a request to select an infrastructure. Responsive to such a request, the infrastructure selection service may determine which infrastructure is appropriate for a particular patient case at hand based on data such as a region associated with the patient case, a doctor or practice associated with the patient case, a product (e.g., treatment type) requested for the patient case, a patient type, and so on. Logic (e.g., one or more machine learning models and/or other models) of the selected infrastructure may then process the patient data.

Embodiments further provide a plurality of infrastructures (e.g., machine learning model infrastructures, medical application infrastructures, etc.), each of which may be or include a cloud-based service and/or medical application that may operate on patient data from a user device of a patient and/or provide treatment information (e.g., dental treatment information) to the user device of the patient and/or to a user device of a doctor based on a result of operating on the patient data. Embodiments also cover systems and methods for modifying the medical application and/or machine learning models of a set of infrastructures (e.g., of a set of machine learning model infrastructures).

Embodiments are discussed with reference to medical applications. It should be understood that such embodiments also pertain to medical software other than medical applications. Accordingly, embodiments discussed herein apply to all types of medical software. Additionally, embodiments are discussed with reference to selection of machine learning model infrastructures. However, it should be understood that embodiments also apply to medical application infrastructure selection. It should, for example, be understood that any discussion of machine learning model infrastructures and machine learning model infrastructure selection also applies to medical application infrastructures and medical application infrastructure selection.

Embodiments are discussed with reference to a machine learning model infrastructure selection service, and to selection of a machine learning model infrastructure. However, it should be understood that embodiments discussed with reference to a machine learning model infrastructure selection service also apply to an infrastructure selection service that selects other type of infrastructures, such as medical application infrastructures, cloud infrastructures, or the like.

FIG. 1A illustrates one embodiment of a system 100 for using an infrastructure selection service (e.g., a machine learning model infrastructure service) 116 to select an infrastructure (e.g., a machine learning model infrastructure) to use for a patient case, in accordance with an embodiment. In one embodiment, the system 100 includes one or more patient computing devices 105, one or more server computing devices 106, 107, one or more data stores 112, and one or more doctor computing devices 108. The patient computing device(s) 105, server computing device(s) 106, 107, data store(s) 112, and doctor computing device(s) 108 may be connected via one or more network 118, which may include one or more private networks (e.g., local area networks (LANs), private wide area networks (WANs) such as Intranets, etc.) and/or public networks (e.g., a public WAN such at the Internet).

The patient computing device(s) 105 may be mobile computing devices (e.g., mobile phones, laptop computers, tablet computers, etc.) and/or traditionally stationary computing devices (e.g., such as desktop computers, game consoles, etc.). The patient computing device(s) 105 may include a medical application 120 installed thereon. The medical application 120 may be a patient-facing medical application. In one embodiment, the medical application 120 is a medical application for virtual care, for remote care, and/or for finding a doctor. In one embodiment, the medical application 120 is a virtual care medical application, such as is described in U.S. Publication No. 2022/0023003, filed Jul. 22, 2021, entitled "Image based dentition tracking," which is incorporated by reference herein in its entirety.

In embodiments, the patient computing device 105 includes an integrated camera or is connected to a camera (e.g., to a webcam). The medical application 120 may include logic for controlling the camera to cause the camera to capture one or more patient images (also referred to herein as medical images). The medical application 120 may direct a user of the patient computing device 105 as to how to position themselves in front of the camera to capture one or more patient images 145. For example, if the medical application 120 is a virtual dental care medical application, then medical application 120 may direct the patient to show their teeth in a smile from one or multiple viewpoints of the camera relative to the patient. The patient may be directed to capture images of their smile (e.g., of their dentition, teeth, gums, etc.) with and/or without one or more dental appliances being worn by the patient. For example, if the medical application 120 is a virtual care application for orthodontic treatment, the patient may be instructed to wear an orthodontic aligner (e.g., which may be a clear plastic aligner) associated with a current stage of treatment, and to take one or more patient images 145 showing the patient's teeth with the orthodontic aligner on the patient's teeth. In some embodiments, the patient is provided with one or more cheek retractors, which the patient may wear during image capture to retract their cheeks and increase an amount of teeth that are shown in captured images. In some embodiments, the medical application 120 is the "My Invisalign" application provided by Align Technology®, Inc.

The patient may additionally or alternatively input one or more patient case details via the medical application 120. For example, the patient may enter their name, gender, age, dental problems and/or concerns (e.g., pain, inflammation, discomfort, etc.). Alternatively, or additionally, the medical application 120 may already have one or more patient case details stored thereon. Examples of patient case details include a patient name, age, gender, doctor, treatment type, location (e.g., region or country or residence), ethnicity, stage of treatment, and so on.

The server computing devices 106, 107 may include physical machines and/or virtual machines hosted by physical machines. The physical machines may be rackmount servers, desktop computers, or other computing devices. The physical machines may include a processing device, memory, secondary storage, one or more input devices (e.g., such as a keyboard, mouse, tablet, speakers, or the like), one or more output devices (e.g., a display, a printer, etc.), and/or other hardware components. In one embodiment, one or more the computing device 106, 107 includes one or more virtual machines, which may be managed and provided by a cloud provider system. Each virtual machine offered by a cloud service provider may be hosted on one or more physical machine.

Server computing devices 106, 107 may be connected to one or more data stores 112 either directly or via a network. Data store(s) 112 may include an internal data store, or an external data store that is connected to computing device(s) 106, 107 directly or via a network. Examples of network data stores include a storage area network (SAN), a network attached storage (NAS), and a storage service provided by a cloud provider system. Data store(s) 112 may include one or more file systems, one or more databases, and/or other data storage arrangement. In embodiments, there are multiple data stores 112, which may be located in different regions (e.g., different countries and/or regional blocs of countries).

As mentioned, in some embodiments computing device 105 includes a medical application 120. Additionally, or alternatively, server computing devices 106, 107 may include a medical application 122 (and/or one or more ML model infrastructures, medical application infrastructures, security infrastructures, data infrastructures, and so on for a medical application) and/or doctor computing device 108 may include a medical application 124. In some embodiments, different server computing devices 107 include different infrastructures 150, each of which may be a component of a medical application 122, may itself constitute a medical application, or may include a medical application. In some embodiments, a medical application 122 may include one or more infrastructures 150 as well as an infrastructure selection service 116. In embodiments, medical application 122 is a cloud-based medical application. In one embodiment, medical application 124 is a doctor-facing medical application. In some embodiments, one or more of medical application 120, medical application 122 and/or medical application 124 are combined into a distributed medical application having both patient-facing aspects and doctor-facing aspects.

In one embodiment, one or more of medical applications 120, 122, 124 is a dental and/or orthodontic treatment application. Medical application(s) 120, 122, 124 may perform dental assessment, treatment planning, treatment tracking, and/or treatment assessment, for example, for restorative dentistry and/or for orthodontics in some embodiments. One or more of medical applications 120, 122, 124 may include clinical settings for multiple different products (e.g., for multiple different types of treatments and/or different treatment options), for one or more regions, for one or more doctors, and so on. Medical application 122 may include different versions that run on or that include different infrastructures 150 (e.g., different ML model infrastructures, different security infrastructures, different data infrastructures, different application infrastructures, different cloud infrastructures, and so on). The different versions of medical application 122 may perform the same functions, may include the same clinical settings, may provide the same products, etc., Alternatively, one or more of the different versions of the medical application 122 may include different clinical settings, may provide different products, and/or may perform different functions. In either case, the different versions of the medical application 122 may be located in (or have components located in) different regions and/or be accessible by different doctors in some embodiments. Each infrastructure may include its own underlaying servers (e.g., web application servers, database servers, etc.), storage, hardware, middleware, cloud platforms, container orchestration tools, serverless computing services, application performance monitoring tools, log management tools, configuration management tools, identity and access management (IAM) systems, security information and event management (SEIM) tools, endpoint protection, virtualization platforms, container platforms, medical software versions, and so on.

A treatment planning application may be responsible for generating a treatment plan that includes a treatment outcome for a patient. The treatment plan may include and/or be based on an initial 2D and/or 3D image of a patient's dental arches. For example, the treatment planning application may receive 2D and/or 3D intraoral images (e.g., intraoral scans) of the patient's dental arches, and may stitch the images or scans together to create a virtual 3D model of the dental arches. Alternatively, the treatment planning application may receive a virtual 3D model of a patient's dental arches. In embodiments, the treatment planning application receives a patient record for a patient case, which may include, for example, intraoral scans, medical images, patient case details, 3D models of the patient's upper and/or lower dental arches, and so on.

The treatment planning application may then determine current positions and orientations of the patient's teeth from the virtual 3D model in a patient record and determine target final positions and orientations for the patient's teeth represented as a treatment outcome. The treatment planning application may further determine one or more stages of treatment, and may determine target positions and orientations of the patient's teeth for each of the stages of treatment. The treatment planning application may additionally or alternatively determine one or more dental prosthetics to be used for a patient, such as a bridge, cap, crown, and so on.

With respect to orthodontic treatment, the treatment planning application may generate a virtual 3D model showing the patient's dental arches at the end of treatment as well as one or more virtual 3D models showing the patient's dental arches at various intermediate stages of treatment. Alternatively, or additionally, the treatment planning application may generate one or more 3D images and/or 2D images showing the patient's dental arches at various stages of treatment. The 3D models for any of the steps of treatment may be manipulated using a medical computer aided drafting (CAD) application in embodiments.

By way of non-limiting example, a dental treatment outcome may be the result of a variety of dental procedures. Such dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as implants, crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances. Any of treatment outcomes or updates to treatment outcomes described herein may be based on these orthodontic and/or dental procedures. Examples of orthodontic treatments are treatments that reposition the teeth, treatments such as mandibular advancement that manipulate the lower jaw, treatments such as palatal expansion that widen the upper and/or lower palate, and so on. For example, an update to a treatment outcome may be generated by interaction with a user to perform one or more procedures to one or more portions of a patient's dental arch or mouth.

A treatment plan for producing a particular treatment outcome may be generated by first generating an intraoral scan of a patient's oral cavity. From the intraoral scan a virtual 3D model of the upper and/or lower dental arches of the patient may be generated. A dental practitioner may then determine a desired final position and orientation for the patient's teeth on the upper and lower dental arches, for the patient's bite, and so on. This information may be used by the treatment planning application to generate a virtual 3D model of the patient's upper and/or lower arches after orthodontic treatment. This data may be used to create an orthodontic treatment plan. The orthodontic treatment plan may include a sequence of orthodontic treatment stages. Each orthodontic treatment stage may adjust the patient's dentition by a prescribed amount, and may be associated with a 3D model of the patient's dental arch that shows the patient's dentition at that treatment stage.

In some embodiments, the treatment planning application may receive or generate one or more virtual 3D models, virtual 2D models, 3D images, 2D images, or other treatment outcome models and/or images, which may be based on intraoral images or scans. For example, an intraoral scan of the patient's oral cavity may have been performed to generate an initial virtual 3D model of the upper and/or lower dental arches of the patient. The treatment planning application may then determine a final treatment outcome based on the initial virtual 3D model, and then generate a new virtual 3D model representing the final treatment outcome. The treatment planning application may additionally determine various intermediate stages of orthodontic treatment, and generate virtual 3D models of the patient's dental arches for each such intermediate stage. Clinically important factors such as an amount of force to be applied to teeth, an amount of rotation to be achieved by teeth, an amount of movement of teeth, teeth interactions, and so on should be considered by the treatment planning application in generation of the intermediate treatment stages.

Once a treatment plan is finalized, the various 3D models of the patient's dental arches for each of the stages of treatment may be used to manufacture orthodontic aligners for each of the stages of treatment. The patient may then wear the orthodontic aligners in order for treatment. At the end of treatment, the patient should have corrected dentition.

One or more medical applications 120, 122, 124 may be treatment tracking and/or assessment applications for orthodontic and/or restorative dentistry. For example, orthodontic treatment may be performed in multiple stages of treatment, as specified in a treatment plan. At any stage of treatment, it may be beneficial for the patient and/or doctor to know whether the patient is responding to treatment as anticipated and/or is on track with regards to the treatment plan. Depending on patient compliance (e.g., how frequently the patient wears his or her orthodontic aligners), patient physiology and/or other factors, teeth may move faster and/or slower than planned. Such information can be important for a doctor to obtain so that the doctor can alter a treatment plan if necessary. One or more medical applications 120, 122, 124 may process patient images 145 and/or patient case details 135 to determine whether an orthodontic aligner fits a patient and/or to track orthodontic treatment of the patient (e.g., to determine whether the patient's teeth have moved as planned according to an orthodontic treatment plan for the patient). In one embodiment, one or more medical applications 120, 122, 124 performs tooth detection and evaluation as set forth in U.S. Pat. No. 10,997,727, issued May 4, 2021, entitled "Deep Learning for Tooth Detection and Evaluation," which is incorporated by reference herein in its entirety.

One or more medical applications 120, 122, 124 may be dental diagnostics applications in embodiments. Dental diagnostics applications may perform one or more analyses of a patient's dentition based on patient information such as 2D images, 3D images, 3D models, patient case details, and so on. The analyses may include an analysis for identifying tooth cracks, an analysis for identifying gum recession, an analysis for identifying tooth wear, an analysis of the patient's occlusal contacts, an analysis for identifying crowding of teeth (and/or spacing of teeth) and/or other malocclusions, an analysis for identifying plaque, an analysis for identifying tooth stains, an analysis for identifying caries, and/or other analyses of the patient's dentition. The dental diagnostics applications may output indications of tooth cracks, gum recession, tooth wear, occlusal contacts, tooth crowding, malocclusions, plaque, tooth stains, caries, and so on, and/or may provide a diagnosis and/or recommended treatment for one or more identified dental conditions. In one embodiment, one or more medical applications 120, 122, 124 performs dental diagnostics as set forth in U.S. Patent Publication No. 2022/0202295, published Jun. 30, 2022, entitled "Dental Diagnostics Hub," which is incorporated by reference herein in its entirety.

In embodiments, medical application 122 uses one or more patient images 145 and/or patient case details 135 to perform treatment tracking, an assessment of a patient's teeth, and/or other operations. The patient case details 135 may include, for example, a doctor identification for a doctor or medical practice treating the patient, a region, a treatment type (e.g., a selected product), a patient type (e.g., one or more features of the patient), and so on. Patient type may include, for example, an adult patient, a teen patient, a child patient, a geriatric patient, a patient having certain medical conditions (e.g., high blood pressure), and so on. A region may include a geographic region, a regional bloc of countries, a state and/or a country region. For example, a region may include U.S.A., California, Maryland, Minnesota, Europe, Germany, France, China, Australia, and so on. A treatment type may include, for example, orthodontic treatment of type 1 malocclusion, orthodontic treatment of type 2 malocclusion, orthodontic treatment of type 3 malocclusion, filling, bridge, cap, dentures, all-on-four treatment, and so on. One example of a treatment type is an orthodontic treatment type.

Medical application 120 may guide a patient to generate patient images 145 of their dentition (e.g., of their smile showing teeth). Medical application 120 provides the patient images 145 and/or patient case details 135 to medical application 122 for processing. In some embodiments, medical application 120 includes an application programming interface (API) for calling medical application 122. Via the API, medical application 120 may call ML model infrastructure selection service 116.

Infrastructure selection service 116 may process patient case details 135 to determine an infrastructure 150 to select from among a plurality of available infrastructures 150. Infrastructure selection service 116 may additionally determine a data store to use to store patient images 145. In some embodiments, each infrastructure 150 has its own dedicated data store 112. Alternatively, one or more different infrastructures 150 may share a data store 112. Data stores 112 are shown as being distinct from ML model infrastructures 150. However, in some embodiments, infrastructures 150 include data stores 112. In some embodiments, medical application 120 includes logic for selecting an infrastructure 150 and/or a data store 112, and such operations are not performed by infrastructure selection service 116 or infrastructure selection service 116 is integrated into medical application 120).

In embodiments, different infrastructures 150 may be set up for different regions (e.g., for different countries and/or regional blocs of countries), for different practice groups (e.g., for different dental practices), for different types of medical applications 122 (e.g., for orthodontic treatment planning applications, treatment tracking applications, dental assessment applications, and so on), for different types of logic (e.g., different types of machine learning models such as deep learning models, generative models, reinforcement learning models, and so on), etc. Each infrastructure may include one or more dedicated servers, data stores, processors, memory, storage, virtual machines, network resources, and/or other infrastructure for running a medical application 122 or one or more components of a medical application 122. In embodiments, each infrastructure includes or hosts one or more trained machine learning models and optionally infrastructure for training additional ML models and/or retraining the one or more trained ML models of the ML model infrastructure 150.

In some embodiments, different regions have their own dedicated infrastructure 150 (or multiple dedicated infrastructures 150). Additionally, different regions may have their own dedicated data store 112 associated with a particular infrastructure 150 of that region. In an example, a first infrastructure 150 (and optionally data store 112) may be located on servers running in the US and may be used to serve patients in the US, a second infrastructure 150 (and optionally data store 112) may be located on servers running in Canada and may be used to serve patients in the Canada, a third infrastructure 150 (and optionally data store 112) may be located on servers running in Europe and may be used to serve patients in the European Union, a fourth infrastructure 150 (and optionally data store 112) may be located on servers running in the China and may be used to serve patients in the China, and so on. ML models 155, applications, logic, models, etc. running in different infrastructures 150 may be the same or may be different. For example, different infrastructures may have different versions of the same trained ML model 155 (e.g., if one country's regulatory body has approved a newest version of the ML model but another country's regulatory body has not yet approved the newest version of the ML model). In another example, different infrastructures may have trained ML models 155 trained to perform different operations (e.g., a first ML model of a first ML model infrastructure may be trained to perform one or more operations for treatment planning and a second ML model of a second ML model infrastructure may be trained to perform one or more operations of treatment tracking). In another example, different infrastructures 150 may include different types of ML models 155 (e.g., one ML model infrastructure 150 may include classification models, another infrastructure 150 may include generative models, another infrastructure 150 may include natural language models, and so on).

Once an infrastructure 150 has been selected, infrastructure selection service 116 (or medical application 120) may send a message to the selected infrastructure 150 to cause one or more ML models 155 and/or other logic of the infrastructure 150 to process the patient images 145 and/or patient case details 135. In one embodiment, infrastructure selection service 116 uses an API of the selected infrastructure to send the message to the infrastructure. In some embodiments, the message to the selected infrastructure 150 includes an address (e.g., a link) to a storage location, in data store 112, of the patient image(s) 145 to be processed. In some embodiments, multiple versions of one or more patient images are stored, including a high resolution version, a medium resolution version, a low resolution version and/or a thumbnail version. One or more of these versions of the image(s) may be retrieved by the infrastructure and processed.

Storage and communication logic 157 of the selected infrastructure 150 may retrieve the patient images 145 from data store 112 and/or otherwise receive the patient images 145 (e.g., patient computing device 105 may send the patient images 145 to the selected infrastructure 150). The ML model(s) 155 and/or other logic may then process the patient image(s) 145 and/or patient case details 135 to generate one or more outputs. In some embodiments, storage and communication logic 157 may additionally retrieve or receive a treatment plan 147 for the patient. The retrieved data may include, for example, a 3D model of an upper and/or lower dental arch of the patient for a current stage of orthodontic treatment. In some embodiments, the ML model(s) 155 and/or other logic of the selected infrastructure 150 processes the patient image(s) 145, patient case details 135 and/or treatment plan 147 to generate an output.

The output generated by the ML model(s) 155 and/or other logic (e.g., rules-based logic) may depend on the nature of the medical application 122, and may include image level classification, pixel level classification, patch level classification, pixel level segmentation, patch level segmentation, generation of overlays, medical assessments, treatment information, and so on. For example, ML model(s) 155 may perform pixel-level segmentation of patient image(s) 145 into one or more objects, such as aligners, teeth, gingiva, and so on. The ML model(s) 155 and/or rule-based logic 156 of the selected infrastructure 150 may process the output of the ML model(s) 155 and/or other logic to generate a further or updated output. The further or updated output may include a visual overlay for the patient image(s) 145, which may include indications of different segments, objects, classes, etc. output by the ML model(s) 155 and/or other logic. In one embodiment, rule-based logic 156 or an ML model 155 performs one or more operations to measure features or objects of the patient image(s) 145 that were identified in the output of the ML model(s) 155. For example, rule-based logic 156 or an ML model 155 may determine distances between edges of an aligner and tooth edges in a patient image 145, and may generate a fit score based on the distances. The fit score may indicate how well the aligner fits the patient's teeth, and may be an indication of how well the patient's teeth are tracking a planned tooth progression of a treatment plan 147. In one embodiment, ML model(s) 155 and/or rule-based logic 156 perform a comparison between a 3D model of an upper and/or lower dental arch for a current stage of treatment in a treatment plan 147 with a patient's dentition as shown in patient image(s) 145. Based on such comparison, ML model(s) 155 and/or other logic may determine a difference between where the patient's teeth were expected to be at the current stage of treatment and where the patient's teeth actually are at the current stage of treatment. ML model(s) 155 and/or rule-based logic 156 may measure distances between points on teeth in patient image(s) 145 and points on the teeth in the 3D model, and determine a deviation from a planned progress based on the distances. In some embodiments, ML model(s) 155 and/or rule-based logic 156 generates a graphical overlay for patient image(s) 145 showing a comparison of where the teeth are in the patient image(s) 145 and where the teeth should be for the current stage of treatment.

In embodiments, one or more trained ML models 155 and/or other logic are used to process patient image(s) 145, patient case details 135 and/or data from a treatment plan 147. The trained ML models may additionally or alternatively include physics models (e.g., that apply finite element analysis). In one embodiment, a single model may be used to perform multiple different analyses (e.g., to identify any combination of tooth cracks, gum recession, tooth wear, occlusal contacts, crowding and/or spacing of teeth and/or other malocclusions, plaque, tooth stains, and/or caries, to identify a fit of an aligner, to generate a treatment plan, to determine how a patient's teeth are on track with regards to a treatment plan, and so on). Additionally, or alternatively, different models may be used to identify different dental conditions, determine a fit of an aligner, determine an amount of deviation of the patient's teeth positions and/or orientations from planned positions and/or orientations of the teeth according to a treatment plan, generate a treatment plan, and so on.

In one embodiment, patient image(s) 145 from one or more points in time are input into one or more trained machine learning models 155 and/or other logic that have been trained or programmed to receive the patient image(s) 145 as an input and to output classifications of one or more types of dental conditions. In one embodiment, patient image(s) 145 from one or more points in time are input into one or more trained machine learning models 155 that have been trained to receive the patient image(s) 145 as an input and to output segmentation information identifying tooth edges and/or aligner edges in the patient image(s) 145, which may be further processed by rule-based logic 156 to measure distances between tooth edges and aligner edges. In one embodiment, patient image(s) 145 from one or more points in time and a 3D model of a dental arch or 2D projections of the 3D model are input into one or more trained machine learning models 155 that have been trained to receive the patient image(s) 145 and a 3D model or 2D projections as an input and to output an indication of deviation between current tooth positions and planned tooth positions.

Embodiments are discussed with regards to processing of patient image(s) 145 generated by a patient computing device 105. However, in some embodiments patient images 145 may be generated by a doctor computing device 108 or by a medical imaging device (not shown), and may be provided to medical application 122 by doctor computing device 108. Such patient image(s) 145 may include other image modalities other than 2D images. For example, such patient images 145 may include intraoral data such as one or more 3D models of a dental arch generated based on an intraoral scan of the patient's oral cavity, one or more projections of one or more 3D models of a dental arch onto one or more planes (optionally comprising height maps), one or more x-rays of teeth of the patient, one or more CBCT scans of the teeth, a panoramic x-ray of the teeth, near-infrared and/or infrared imaging data, color image(s), ultra-violet imaging data, intraoral scans, and so on. If data from multiple imaging modalities are used (e.g., 3D scan data, color images, and NIRI imaging data), then the data may be registered and/or stitched together so that the data is in a common reference frame and objects in the data are correctly positioned and oriented relative to objects in other data. One or more feature vectors may be input into the trained ML model 155 and/or other models or logic, where the feature vectors include multiple channels of information for each point or pixel of an image. The multiple channels of information may include color channel information from a color image, depth channel information from intraoral scan data, a 3D model or a projected 3D model, intensity channel information from an x-ray image, and so on.

The trained machine learning model(s) 155 and/or other logic may process patient image(s) 145 and output object classification, pixel-level segmentation, etc. In one embodiment, trained ML model 155 outputs a probability map, where each point in the probability map corresponds to a point in the patient image(s) 145 and indicates probabilities that the point represents one or more dental classes. In one embodiment, a single model outputs probabilities associated with multiple different types of dental classes, which may include one or more dental condition classes. In an example, a trained machine learning model may output a probability map with probability values for a teeth dental class and a gums dental class. The probability map may further include probability values for tooth cracks, an aligner class, gum recession, tooth wear, occlusal contacts, crowding and/or spacing of teeth and/or other malocclusions, plaque, tooth stains, healthy area (e.g., healthy tooth and/or healthy gum) and/or caries.

In some instances, multiple machine learning models are used, where each machine learning model identifies a subset of the possible dental conditions and/or classes. For example, a first trained machine learning model may be trained to output a probability map with three values, one each for teeth, gums, and aligner. Alternatively, the first trained machine learning model may be trained to output a probability map with two values, one each for healthy teeth and caries. One or more additional trained machine learning models may each be trained to output probability maps associated with identifying specific types of dental conditions.

The output of the one or more trained machine learning models may be used to update or generate a visual overlay for one or more patient image(s) 145. In one embodiment, a different layer is generated for each dental class. A layer may be turned on to graphically illustrate areas of interest on the upper and/or lower dental arch that belong to the dental class.

In embodiments, rule-based logic 156 performs image processing and/or 3D data processing on the patient image(s) 145 and/or on an output of one or more trained ML models 155. Such image processing and/or 3D data processing may be performed using one or more algorithms. For example, a trained model may identify tooth edges and aligner edges, and image processing may be performed to assess the fit of the aligner on the patient teeth based on the tooth edges and the aligner edges (e.g., based on measured distances between the aligner edges and the tooth edges). The image processing may include performing automated measurements such as size measurements, distance measurements, amount of change measurements, rate of change measurements, ratios, percentages, and so on. Accordingly, the image processing and/or 3D data processing may be performed to determine severity levels of dental conditions identified by the trained model(s), of a deviation between a planned tooth position and an actual tooth position, and so on.

The one or more trained machine learning models 155 may be support vector machines, random forest models, Bayesian classifiers, regression models, neural networks such as deep neural networks or convolutional neural networks, generative models, and so on. ML models 155 may be trained for image based classification, semantic classification, and so on. Some ML models 155 may be or include generative models, such as generative adversarial networks (GANs). ML models 155 may include machine learning models trained using supervised training and/or ML models trained using unsupervised learning. In some embodiments, one or more ML models 155 are reinforcement learning models.

Artificial neural networks (e.g., deep neural networks and convolutional neural networks) generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize that the image contains a face or define a bounding box around teeth in the image. Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited.

Training of a neural network may be achieved in a supervised learning manner, which involves feeding a training dataset including labeled inputs through the network, observing its outputs, defining an error (by measuring the difference between the outputs and the label values), and using techniques such as deep gradient descent and backpropagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

To train the one or more machine learning models 155, a training dataset (or multiple training datasets, one for each of the machine learning models to be trained) containing hundreds, thousands, tens of thousands, hundreds of thousands or more images should be used to form a training dataset. In embodiments, up to millions of cases of patient dentition that include one or more labeled dental classes are used. The machine learning models may be trained to automatically classify and/or segment patient image(s) 145, and the segmentation/classification may be used to automatically determine aligner fit, orthodontic treatment progress, presence and/or severity of dental conditions, and so on.

A training dataset may be gathered, where each data item in the training dataset may include an image and an associated label (e.g., indicating different objects in the image). Additional data may also be included in the training data items. Accuracy of segmentation can be improved by means of additional classes, inputs and multiple views support. Multiple sources of information can be incorporated into model inputs and used jointly for prediction. Multiple dental classes can be predicted concurrently from a single model in some embodiments. Multiple problems can be solved simultaneously: teeth/gums segmentation, dental condition classification, etc.

The result of this training is a function that can perform dental object classification and/or segmentation, predict dental classes, etc. directly from patient images 145 and/or other intraoral data or patient case details 135. In some embodiments, the machine learning model(s) may be trained to generate a probability map, where each point in the probability map corresponds to a pixel of an input image and/or other input intraoral data and indicates one or more of a first probability that the pixel represents a first dental class, a second probability that the pixel represents a second dental class, a third probability that the pixel represents a third dental class, a fourth probability that the pixels represents a fourth dental class, a fifth probability that the pixel represents a fifth dental class, and so on.

Once ML model(s) 155 have processed patient image(s) 145, patient case details 135 and/or a treatment plan 147 to generate an output, and optionally rule-based logic 156 has optionally processed the output to generate a further or updated output, storage and communication logic 157 may provide the patient image(s) 145, output and/or further or updated output to a doctor computing device 108 of a doctor for the patient. The output of the ML model(s) 155 and/or the further and/or updated output of the rule-based logic 155 may include dental treatment information in embodiments. The dental treatment information 155 may include aligner fit information, treatment plan tracking information (e.g., indicating a deviation of positions of patient teeth from planned positions of the patient teeth), dental conditions, and so on.

Doctor computing device 108 may receive the patient images 145, output, and/or updated or further output (e.g., dental treatment information 155). Doctor computing device 108 may be a mobile computing device or a traditionally stationary computing device. A medical application 124 executing on the doctor computing device 108 may present the patient image(s) 145, dental treatment information 155, patient case details 135 and/or information for the treatment plan 147 on a display of doctor computing device 108. The doctor may then review the presented information and determine, for example, whether to modify a treatment plan, whether to bring in the patient for an in-person visit, and so on. The medical application 124 may be or include a treatment planning application, a treatment management application, a case assessment application, a treatment tracking application, dental practice management software (DPMS), and/or other doctor-facing medical application 124. Medical application 124 may enable a doctor to review submitted cases and/or dental treatment information, manage treatment plans, review intraoral scans, 3D models and/or treatment plans, select and/or approve treatment plans, track treatment progress, and so on. In one embodiment, medical application 124 corresponds to and/or includes the Invisalign Doctor Portal and/or ClinCheck software provided by Align Technology®, Inc.

In some embodiments, the dental treatment information 155 is additionally or alternatively sent to patient computing device 105 for patient review. In some embodiments, rather than executing on doctor computing device 108, medical application 124 is a cloud-based application, and may be part of medical application 122. Doctor computing device 108 may access the medical application 124 in that case using, for example, a web browser.

Figure 1B:
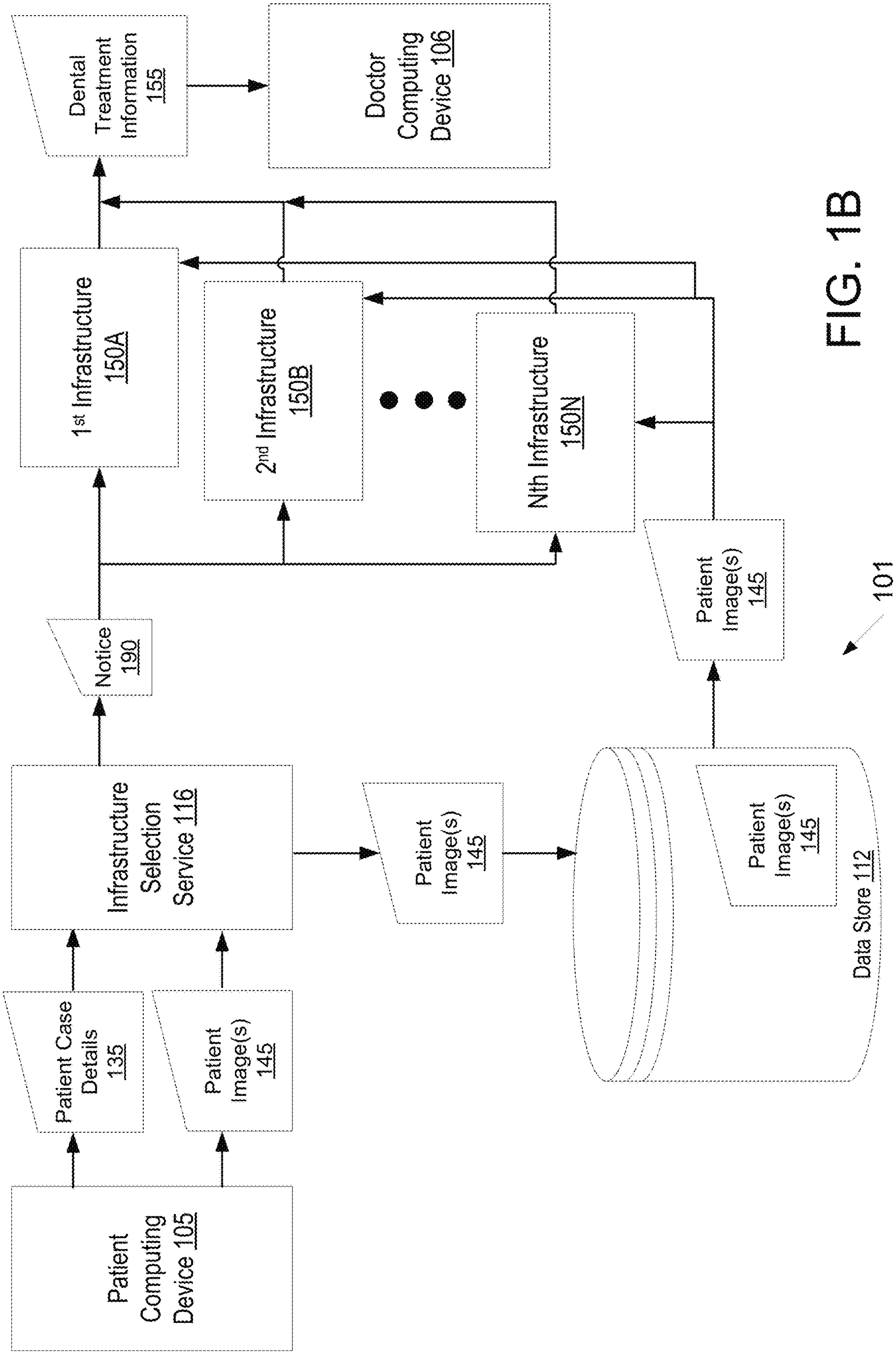
FIG. 1B illustrates one embodiment of selecting and using a machine learning model infrastructure or other type of infrastructure for a medical application, in accordance with an embodiment.

FIG. 1B illustrates one embodiment of a sequence of operations 101 for selecting and using an infrastructure (e.g., a machine learning model infrastructure) for a medical application, in accordance with an embodiment.

In one embodiment, a patient computing device 105 provides patient case details 135 and one or more patient image(s) 145 to an infrastructure selection service 116. The infrastructure selection service 116 may select an infrastructure from among multiple available infrastructures (e.g., first infrastructure 150A, second infrastructure 150B, through nth infrastructure 150N) to use for processing of the patient image(s) 145 based, at least in part, on one or more of the patient case details 135, such as location, doctor, patient type, and so on. Infrastructure selection service 116 may cause the patient image(s) 145 to be stored in a data store 112. In some embodiments, a data store 112 for storage of the patient image(s) 145 is selected along with the infrastructure. In some embodiments, first infrastructure 150A, second infrastructure 150B, through nth infrastructure 150N are machine learning model infrastructures.

The selected infrastructure 150A-N may receive the patient image(s) 145 (e.g., may retrieve the patient image(s) 145 from the data store 112, and may process the patient image(s) to generate an output including dental treatment information 155. The dental treatment information 155 may be provided to a doctor computing device 106 for review.

Figure 2:
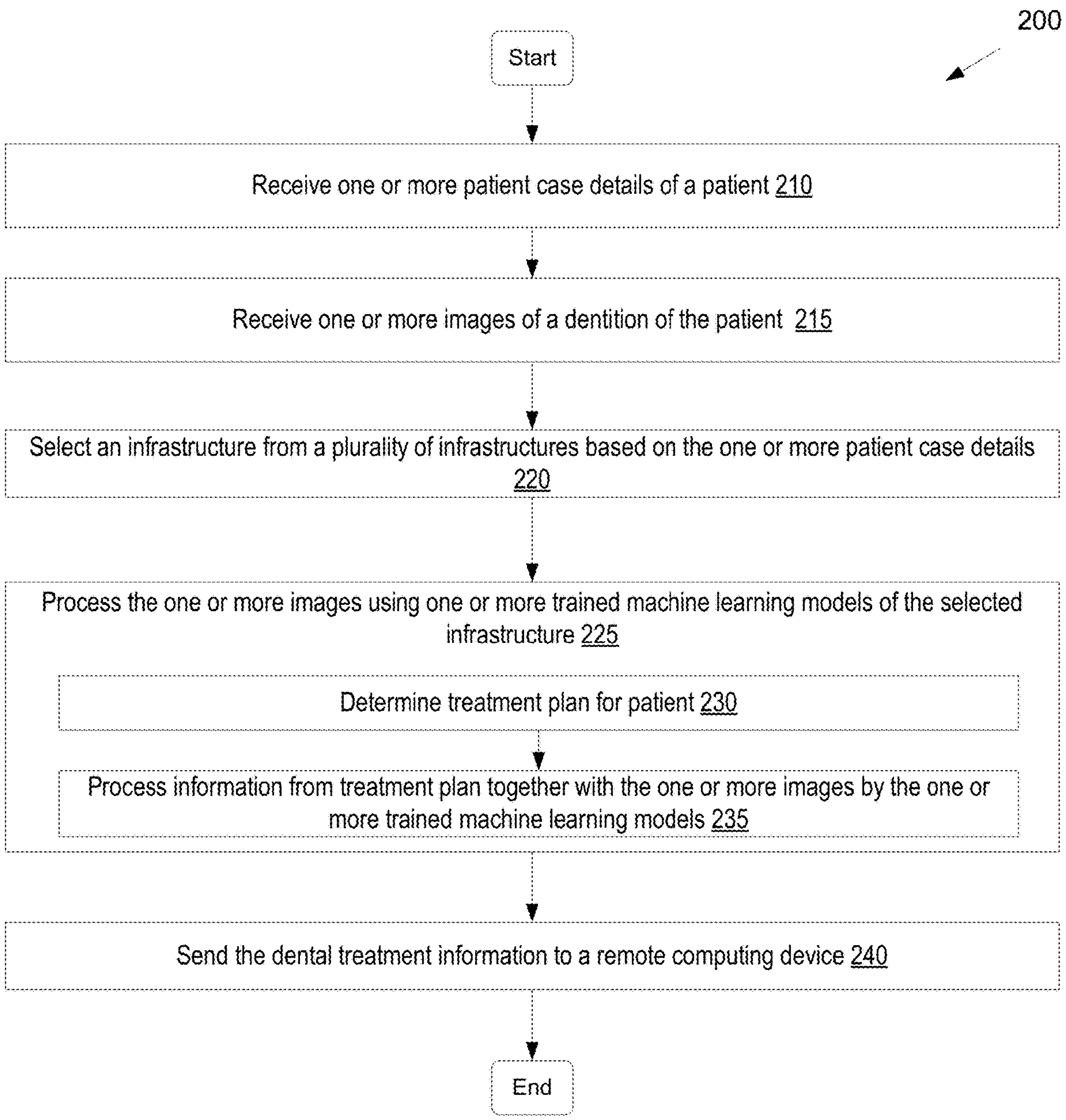
FIG. 2 illustrates a flow diagram for a method of selecting and using a machine learning model infrastructure, in accordance with an embodiment.
Figure 3:
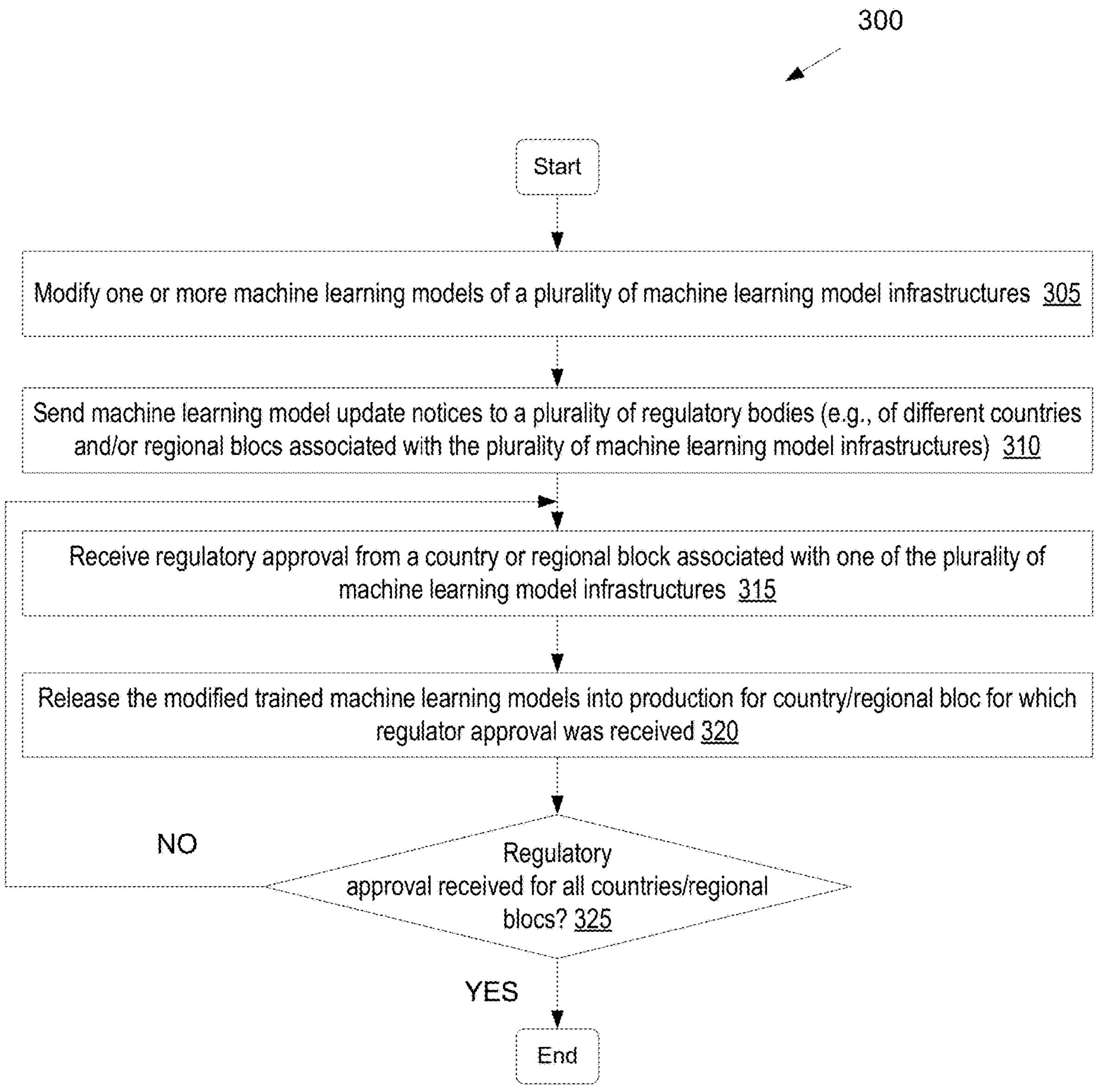
FIG. 3 illustrates a flow diagram for a method of updating one or more machine learning model infrastructures, in accordance with an embodiment.

FIGS. 2-3 below describe methods associated with selection, training and/or use of ML model infrastructures. Though discussed with reference to ML models infrastructures, embodiments also apply to selection and/or use of other types of infrastructures. The methods depicted in FIGS. 2-3 may be performed by a processing logic that may comprise hardware (e.g., circuitry, dedicated logic, programmable logic, microcode, etc.), software (e.g., instructions run on a processing device), or a combination thereof. In embodiments, one or more of the methods are performed by a computing device such as computing device 400 of FIG. 4.

FIG. 2 illustrates a flow diagram for a method 200 of selecting and using a machine learning model infrastructure, in accordance with an embodiment. At block 210 of method 200, processing logic receives one or more patient case details of a patient. The patient case details may include a patient location, a doctor or practice identifier, a patient type (e.g., based on patient age), a treatment plan identifier, a treatment type (e.g., orthodontic or prosthodontic treatment), a stage of treatment, and so on. At block 215, processing logic may additionally receive one or more images of a dentition of the patient. The patient case details and/or images may be received from a patient computing device in embodiments. In some embodiments, operations 210 and 215 are performed by a logic of a cloud-based service. In some embodiments, operations 210 and/or 215 are performed by logic of a patient computing device. For example, a patient may capture the one or more images using the computing device.

At block 220, processing logic selects a machine learning model infrastructure from a plurality of available machine learning model infrastructures based at least in part on the one or more patient case details using one or more ML model infrastructure selection rules. For example, the patient case details may include a patient location, and processing logic may select an ML model infrastructure assigned to a region that includes the location of the patient. In some embodiments, the patient case details include a patient type, and the ML model infrastructure is selected based on the patient type. For example, a first ML model infrastructure may be for children and a second ML model infrastructure may be for adults. In some embodiments, the patient case details include a doctor identifier or practice identifier of a doctor/practice treating the patient, and the ML model infrastructure is selected based on the doctor or practice identifier. For example, some large dental practices may include their own dedicated ML model infrastructure that is not used for other dental practices. The ML models for the practice may be tailored to the preferences of that dental practice, and may differ from default settings of ML model infrastructures used for other dental practices. In some embodiments, an ML model infrastructure is selected based on a combination of patient case details, such as region, doctor identifier and patient type. For example, there may be different sets of ML model infrastructures for different regions. A set of ML model infrastructures may be determined based on the patient's location. A particular ML model infrastructure from the determined set may be determined based on other patient case details such as doctor identifier and/or patient type.

At block 225, processing logic processes the one or more images using one or more trained machine learning models of the selected ML model infrastructure. This may include providing the image(s) to the ML model infrastructure, and then processing the image(s) using processing logic of the ML model infrastructure. In one embodiment, at block 230 processing logic determines a treatment plan for the patient. At block 235, processing logic then processes information from the treatment plan (e.g., a 3D model of an upper and/or lower dental arch from the treatment plan corresponding to a current stage of orthodontic treatment of the patient) and the one or more images using the one or more trained machine learning models of the selected ML model infrastructure. As a result of processing the image(s) and/or treatment plan information (e.g., a 3D model or projection(s) of the 3d model onto one or more planes corresponding to planes of the one or more images), the ML model(s) may output dental treatment information. Alternatively, or additionally, the ML model(s) may output dental classification and/or segmentation information for the image(s). The image(s) with segmented or labeled objects may be further processed (e.g., using one or more image processing algorithms) to determine dental treatment information in some embodiments, such as an aligner fit, an orthodontic treatment progress report, one or more dental conditions, and so on.

In one embodiment, the dental treatment information comprises orthodontic treatment information, such as aligner fit, differences between planned tooth positions and actual tooth positions for a stage of orthodontic treatment, information identifying whether or not an orthodontic treatment is progressing as planned, an indication that one or more teeth are moving as planned or are moving slow than planned, and so on. In one embodiment, the one or more images of the patient comprise images of the patient wearing an orthodontic aligner, and the selected machine learning model infrastructure determines one or more edges of the orthodontic aligner, determines one or more edges of teeth of the patient, and determines one or more distances between the one or more edges of the orthodontic aligner and the one or more edges of the teeth. The dental treatment information may then comprise an overlay for the one or more images indicating the one or more edges of the teeth, the one or more edges of the orthodontic aligner, and the one or more distances. In one embodiment, the one or more machine learning models perform assessments of the dentition of the patient (in the images) with respect to a plurality of dental conditions, the plurality of dental conditions comprising at least one of caries, gum recession, tooth wear, malocclusion, tooth crowding, tooth spacing, plaque, tooth stains, or tooth cracks.

At block 240, processing logic may send the dental treatment information and/or images to a remote computing device. The remote computing device may be, for example, a remote computing device of a doctor or medical practice indicated in the patient case details. The doctor may then review the dental treatment information and make one or more assessments, schedule an in-person patient visit, etc. based on the dental treatment information.

FIG. 3 illustrates a flow diagram for a method 300 of updating one or more machine learning model infrastructures, in accordance with an embodiment.

At block 305 of method 300, one or more machine learning models of a plurality of machine learning model infrastructures is modified. For example, further training may be performed on an ML model that is installed at multiple ML model infrastructures to refine the ML model. The ML model may be a component of a medical application. Additionally, or alternatively, non-ML aspects of a medical application may be modified.

At block 310, a machine learning model update notice (or medical application update notice) may be sent to a plurality of regulatory bodies of different countries and/or regional blocs associated with the plurality of machine learning model infrastructures. For example, a first ML model infrastructure may be located in a first country having a first regulatory body that governs medical applications and a second ML model infrastructure may be located in a second country having a second regulatory body that governs medical applications.

At block 315, regulatory approval may be received from a country or regional bloc associated with one of the plurality of machine learning model infrastructures. At block 320, the modified ML model(s) (or otherwise modified medical applications) may be related into production for the country or regional bloc for which the regulatory approval was received. This may include replacing an existing version the ML model with the modified version of the ML model in the ML model infrastructure associated with the country or regional bloc. Since different ML model infrastructures are used for different jurisdictions, approval from all regulatory bodies is not necessary before releasing the updated ML models into production for any of the other jurisdictions. Accordingly, as regulatory approval is received in each individual region, the updated ML model may be released into production for that region.

At block 325, processing logic may determine whether regulatory approval has been received for all countries/regional blocs associated with ML model infrastructures. If so, the method ends. If not, the method returns to block 315.

Figure 4:
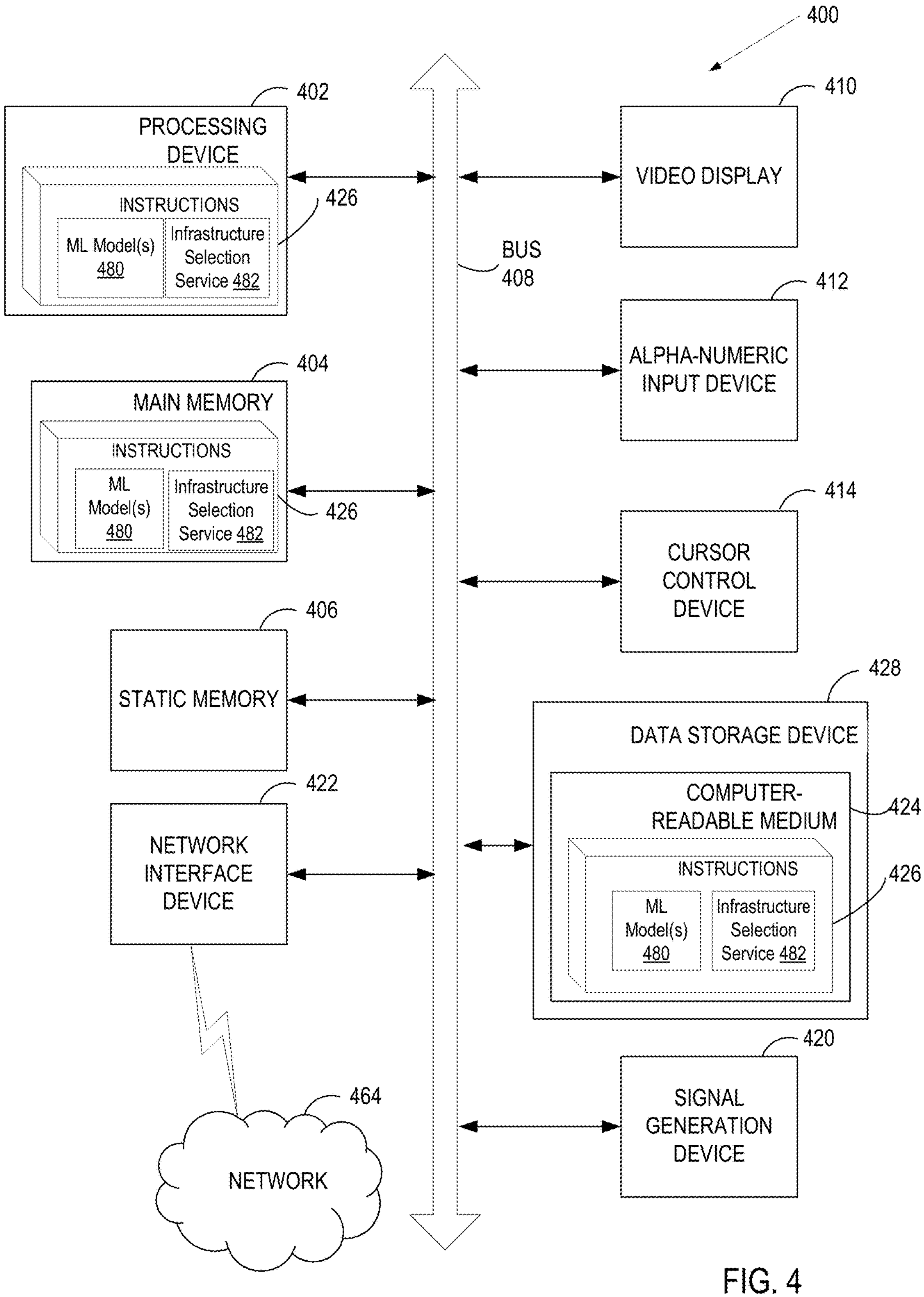
FIG. 4 illustrates a block diagram of an example computing device, in accordance with embodiments of the present disclosure.

FIG. 4 illustrates a diagrammatic representation of a machine in the example form of a computing device 400 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a personal digital assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computer device 400 corresponds to any of computing device 105, 106, 107 and/or 108 of FIG. 1A.

The example computing device 400 includes a processing device 402, a main memory 404 (e.g., read-only memory (ROM), flash memory, dynamic random access memory (DRAM) such as synchronous DRAM (SDRAM), etc.), a static memory 406 (e.g., flash memory, static random access memory (SRAM), etc.), and a secondary memory (e.g., a data storage device 428), which communicate with each other via a bus 408.

Processing device 402 represents one or more general-purpose processors such as a microprocessor, central processing unit, or the like. More particularly, the processing device 402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 402 may also be one or more special-purpose processing devices such as an application specific integrated circuit (ASIC), a field programmable gate array (FPGA), a digital signal processor (DSP), network processor, or the like. Processing device 402 is configured to execute the processing logic (instructions 426) for performing operations and steps discussed herein.

The computing device 400 may further include a network interface device 422 for communicating with a network 464. The computing device 400 also may include a video display unit 410 (e.g., a liquid crystal display (LCD) or a cathode ray tube (CRT)), an alphanumeric input device 412 (e.g., a keyboard), a cursor control device 414 (e.g., a mouse), and a signal generation device 420 (e.g., a speaker).

The data storage device 428 may include a machine-readable storage medium (or more specifically a non-transitory computer-readable storage medium) 424 on which is stored one or more sets of instructions 426 embodying any one or more of the methodologies or functions described herein, such as instructions for ML models 480 and/or for an infrastructure selection service 482. In embodiments, ML models 480 correspond to ML models of one or more infrastructures, and infrastructure selection service 482 corresponds to infrastructure selection server 116 of FIG. 1A. A non-transitory storage medium refers to a storage medium other than a carrier wave. The instructions 426 may also reside, completely or at least partially, within the main memory 404 and/or within the processing device 402 during execution thereof by the computer device 400, the main memory 404 and the processing device 402 also constituting computer-readable storage media.

The computer readable storage medium 424 may also store a software library containing methods for the ML models 480 and/or the infrastructure selection service 482. While the computer-readable storage medium 424 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A system comprising:

a computing device comprising a memory and one or more processing devices, wherein the computing device is configured to:

receive one or more patient case details of a patient, wherein the patient case details comprise a region, wherein the region comprises a country or a regional bloc of countries in which the patient is located;

receive one or more images of a dentition of the patient;

select an infrastructure from a plurality of infrastructures based at least in part on the one or more patient case details, wherein the selected infrastructure is at least one of: a) compliant with regulations of the country or the regional bloc or b) located in the country or in the regional bloc, wherein the plurality of infrastructures comprise a first infrastructure and a second infrastructure, wherein the first infrastructure is located in a first country or regional bloc and complies with regulations of the first country or regional bloc, and wherein the second infrastructure is located in a second country or regional bloc and complies with regulations of the second country or regional bloc;

process the one or more images using logic of the selected infrastructure, wherein the logic outputs dental treatment information for the patient; and send the dental treatment information to a remote computing device.

2. The system of claim 1, wherein the one or more images and the one or more patient case details are received from a mobile device of the patient, wherein the remote computing device is a computing device of a doctor treating the patient, and wherein the one or more images are also sent to the remote computing device of the doctor.

3. The system of claim 1, wherein the patient case details further comprise at least one of a treatment type, a patient type, or a practice identifier.

4. The system of claim 3, wherein the patient case details comprise the treatment type, and wherein the treatment type is an orthodontic treatment type or a prosthodontic treatment type.

5. The system of claim 3, wherein the patient case details comprise the practice identifier, wherein the practice identifier indicates a dental practice that has its own dedicated machine learning model infrastructure.

6. The system of claim 3, wherein the patient case details comprise the patient type, and wherein the patient type is based on patient age.

7. The system of claim 1, wherein the computing device is further configured to:

modify one or more trained machine learning models of the first infrastructure and of the second infrastructure;

send a machine learning model update notice to a first regulatory body of the first country or regional bloc and to a second regulatory body of the second country or regional bloc;

receive regulatory approval from the first regulatory body; and release the modified one or more trained machine learning models into production for the first infrastructure without first receiving regulatory approval from the second regulatory body.

8. The system of claim 1, wherein the dental treatment information comprises orthodontic treatment information.

9. The system of claim 8, wherein the orthodontic treatment information comprises information identifying whether or not an orthodontic treatment is progressing as planned.

10. The system of claim 9, wherein:

the one or more images of the dentition of the patient comprise images of the patient wearing an orthodontic aligner;

the selected infrastructure is a machine learning model infrastructure that determines one or more edges of the orthodontic aligner, determines one or more edges of teeth of the patient, and determines one or more distances between the one or more edges of the orthodontic aligner and the one or more edges of the teeth; and the dental treatment information comprises an overlay for the one or more images indicating the one or more edges of the teeth, the one or more edges of the orthodontic aligner, and the one or more distances.

11. The system of claim 9, wherein the orthodontic treatment information comprises an indication that one or more teeth of the patient are moving as planned or are moving slower than planned.

12. The system of claim 1, wherein the logic comprises one or more trained machine learning models, and wherein the computing device is further configured to:

determine a treatment plan for the patient; and input information from the treatment plan and the one or more images into the one or more trained machine learning models;

wherein the one or more trained machine learning models perform a comparison of the dentition of the patient from the one or more images to the information from the treatment plan and output one or more estimations based on a result of the comparison.

13. The system of claim 12, wherein the information from the treatment plan comprises at least one of a three-dimensional (3D) model of a dental arch of the patient for a current stage of treatment or one or more projections of the 3D model onto one or more planes that correspond to planes of the one or more images.

14. The system of claim 1, wherein the logic comprises one or more trained machine learning models that perform assessments of the dentition of the patient with respect to a plurality of dental conditions, the plurality of dental conditions comprising at least one of caries, gum recession, tooth wear, malocclusion, tooth crowding, tooth spacing, plaque, tooth stains, or tooth cracks.

15. The system of claim 1, wherein the one or more patient case details are received by an infrastructure selection service that performs the selection of the infrastructure, and wherein the computing device is further configured to:

store the one or more images; and notify, by the infrastructure selection service, the selected infrastructure of a storage location of the one or more images, wherein the selected infrastructure retrieves the one or more images from the storage location.

16. The system of claim 1, wherein the plurality of infrastructures comprise a plurality of different types of trained machine learning models.

17. The system of claim 16, wherein the plurality of different types of trained machine learning models comprise at least one of an image based classifier, a semantic classifier, a generative model, or a convolutional neural network.

18. The system of claim 1, wherein the selected infrastructure is a machine learning model infrastructure selected from a plurality of machine learning model infrastructures, and wherein the logic of the infrastructure comprises one or more trained machine learning models of the machine learning model infrastructure.

19. A non-transitory computer readable medium comprising instructions that, when executed by one or more processing devices, cause the one or more processing devices to perform operations comprising:

receiving one or more patient case details of a patient, wherein the patient case details comprise a region, wherein the region comprises a country or a regional bloc of countries in which the patient is located;

receiving one or more images of a dentition of the patient;

selecting a machine learning model infrastructure from a plurality of machine learning model infrastructures based at least in part on the one or more patient case details, wherein the selected machine learning model infrastructure is at least one of: a) compliant with regulations of the country or the regional bloc or b) located in the country or in the regional bloc, wherein the plurality of machine learning model infrastructures comprise a first machine learning model infrastructure and a second machine learning model infrastructure, wherein the first machine learning model infrastructure is located in a first country or regional bloc and complies with regulations of the first country or regional bloc, and wherein the second machine learning model infrastructure is located in a second country or regional bloc and complies with regulations of the second country or regional bloc;

processing the one or more images using one or more trained machine learning models of the selected machine learning model infrastructure, wherein the one or more trained machine learning models output dental treatment information for the patient; and sending the dental treatment information to a remote computing device.

20. A method comprising:

receiving one or more patient case details of a patient, wherein the patient case details comprise a region, wherein the region comprises a country or a regional bloc of countries in which the patient is located;

receiving one or more images of a dentition of the patient;

selecting an infrastructure from a plurality of infrastructures based at least in part on the one or more patient case details, wherein the selected infrastructure is at least one of: a) compliant with regulations of the country or the regional bloc or b) located in the country or in the regional bloc, wherein the plurality of infrastructures comprise a first infrastructure and a second infrastructure, wherein the first infrastructure is located in a first country or regional bloc and complies with regulations of the first country or regional bloc, and wherein the second infrastructure is located in a second country or regional bloc and complies with regulations of the second country or regional bloc;

processing the one or more images using one or more models of the selected infrastructure, wherein the one or more models output dental treatment information for the patient; and sending the dental treatment information to a remote computing device.

* * * * *